United States Patent [19]

Campbell et al.

[11] Patent Number: 4,526,034
[45] Date of Patent: Jul. 2, 1985

[54] KRYPTON HYGROMETER

[75] Inventors: Gaylon S. Campbell, Pullman, Wash.; Bertrand D. Tanner, Mendon, Utah; Robert V. Gauthier, Rocky Hill, N.J.

[73] Assignee: Campbell Scientific, Inc., Logan, Utah

[21] Appl. No.: 607,750

[22] Filed: May 7, 1984

[51] Int. Cl.³ .................... G01W 1/00; G01N 27/62
[52] U.S. Cl. ................... 73/336.5; 250/504 R
[58] Field of Search .......... 73/336.5, 335, 30; 250/372, 504 R

[56] References Cited

U.S. PATENT DOCUMENTS

| | | |
|---|---|---|
| 2,649,707 | 6/1951 | Donath et al. |
| 3,379,968 | 10/1963 | Yamane |
| 3,454,828 | 7/1966 | Yamane |
| 3,636,768 | 1/1972 | Tinet et al. |
| 4,028,617 | 6/1977 | Kamo et al. |
| 4,114,088 | 9/1978 | Laws |

OTHER PUBLICATIONS

"The Variable-Path Lyman-alpha Hygrometer and Its Operating Characteristics", by Arden L. Buck, *Bulletin of the American Meteorological Society*, vol. 57, No. 9, Sep. 1976 at pp. 1113-1118.
"Water Vapor Measurements Utilitzing the Absorption of Vacuum Ultraviolet and Infrared Radiation", by James E. Tillman; published in *Principles and Methods of Measuring Humidity in Gases*, pp. 428-443, R. E. Ruskin, Editor.
"Humidity Fluctuations Over a Vegetated Surface Measured with a Lyman-alpha Hygrometer and a Fine-Wire Thermocouple Psychorometer", by T. Grayson Redford, Jr., et al. *Journal of Applied Meteorology*, vol. 19, Jul. 1980, pp. 860-867.
"Lyman-alpha Hygrometer Operator's Manual", published by Campbell Scientific, Inc.

Primary Examiner—Stewart J. Levy
Assistant Examiner—Joseph W. Roskos
Attorney, Agent, or Firm—Wells, St. John & Roberts

[57] ABSTRACT

An improved spectroscopic hygrometer includes a krypton-filled source tube that produces emissions at 123.58 nm for selective absorption by water vapor in a gaseous sample. The method for measuring water vapor density requires generation of ultraviolet radiation from a krypton source, receipt of the radiation by a detector, and passage of a gaseous sample through the radiation that is directed to the detector. The krypton radiation has been found to be an effective source for hygrometry purposes, and a practical improvement over prior hydrogen sources.

6 Claims, 5 Drawing Figures 4,526,034

KRYPTON HYGROMETER

FIELD OF THE INVENTION

This disclosure relates to measurement of humidity. It specifically discloses an improvement in hygrometers which measure water vapor density as a function of absorption of ultraviolet radiation.

BACKGROUND OF THE INVENTION

This invention arose from an effort to develop a fast response humidity sensor for data required to calculate the rate of evaporation of water from a crop or soil surface. It followed initial development of a fast-response, ultrasonic anemometer which accurately measures the vertical component of the wind. When this anemometer was used with a fine-wire thermometer, one could determine the departures of temperature and vertical wind from their mean values. By accumulating the product of these departures over a time period one could effectively measure the flux of heat above crop and soil surfaces.

A logical extension of this instrumentation was the development of a fast-response humidity sensor. Fluctuations in atmospheric moisture, multiplied by fluctuations in vertical wind, provide a calculation of the rate of evaporation of water from a crop or soil surface. However, the humidity sensor used in such measurements must have a fast-response, be very sensitive to changes in atmospheric moisture, operate reliably from battery power so as to be portable, be sufficiently durable for field operations, and have a stable calibration. Several humidity sensors had been designed to measure water vapor fluctuations, but none of them met all of these requirements.

It was concluded that an ultraviolet hygrometer, using a hydrogen source tube and a nitric oxide detector, would come closest to meeting the requirements listed above. However, no commercially available instrument could be operated by use of battery power.

These project needs led to the design of a low power Lyman-alpha hygrometer. The background of such instruments is generally described in the following three articles, which are hereby incorporated within this disclosure by reference:

"The Variable-Path Lyman-alpha Hygrometer and Its Operating Characteristics", by Arden L. Buck. *Bulletin of the American Meteorological Society*, Volume 57, No. 9, September, 1976, at pages 1113-1118.

"Water Vapor Measurements Utilizing the Absorption of Vacuum Ultraviolet and Infrared Radiation", by James E. Tillman; published in *Principles and Methods of Measuring Humidity in Gases*, pages 428-443, R. E. Ruskin, Editor.

"Humidity Fluctuations Over a Vegetated Surface Measured with a Lyman-alpha Hygrometer and a Fine-Wire Thermocouple Psychrometer" by T. Grayson Redford, Jr. et al, *Journal of Applied Meteorology*, Volume 19, July, 1980, pages 860-867.

As a result of this development, a low power Lyman-alpha hygrometer was designed, using commercial source and detector tubes and a conventional, open path arrangement so that air could move freely between the source and detector. The open path was between 0.5 and 1.0 cm in length, depending upon ambient moisture conditions. It is commercially available from Campbell Scientific, Inc. of Logan, Utah and is identified as Model 220. Its operation is discussed in the "Lyman-alpha Hygrometer Operator's Manual" published by Campbell Scientific, Inc., which is also hereby incorporated within this disclosure by reference.

The Model 220 Lyman-alpha Hygrometer has been sufficiently sensitive for accurate measurement purposes, has adequately fast-response, and operates satisfactorily from a battery power source. While this hygrometer has been in successful operation since its design in 1978, inherent shortcomings in its components have prompted continual further research and development. Most serious was the fact that calibration of the instrument was not stable over time. In addition, the source and detector tubes originally used in the instrument were not adequately reliable or rugged. They often required replacement during the course of experiments, at considerable expense in both time and money.

There were two reasons for these problems. One was that the seals between the magnesium fluoride windows and the glass tubes used as the source and detector were sometimes defective. While this is a particularly difficult seal to construct, the problem was cured by locating a source of tubes incorporating a special glass frit seal. This cured the problems of tube field reliability and durability. However, the calibration difficulties and degradation of source tube strength were inherent in the use of hydrogen as the filling gas in the source tube.

Hydrogen, in the excited state, is very reactive. During use of the hygrometer, the hydrogen emits ultraviolet radiation at the Lyman-alpha wavelength and also reacts chemically with the electrodes. It is therefore used up over a period of time. In order to extend tube life, they often are filled with a greater supply of hydrogen than is necessary for optimum performance. This higher gas pressure inside the tube contaminates the resulting spectrum with radiation at many undesired wavelengths in addition to the desired Lyman-alpha line. Such contamination produces results that do not follow Beer's simple law, which makes the calibration of the instrument then more complex.

We were able to deal with these complexities, and to obtain usable calibration data. However, the most serious difficulty encountered remained the fact that as the hydrogen was used, the radiation spectrum changed, resulting in changes in instrument calibration. The hygrometer was usable, but not ideal.

Two approaches have been tried by others to correct this operating deficiency inherent in all Lyman-alpha hygrometers. In the article by Buck, cited above, there is a description of the use of uranium hydride in the hydrogen source tube. When heated to the appropriate operating temperature, the presence of uranium hydride controls the hydrogen pressure inside the tube to maintain it at the correct value so that a very pure Lyman-alpha line is emitted. The hydride replaces hydrogen as it is used up at the electrodes. However, this approach presented two problems in the design of our portable hygrometer. First, the tubes were very expensive. Second, the heater needed to control the temperature of the hydride used too much power for battery operation.

The second known approach is to excite the hydrogen by using microwaves from outside the tube, thereby eliminating the need for electrodes within the tube. While such tubes are commercially available and do emit very pure Lyman-alpha radiation, they are very expensive and again consume too much power for a portable unit.

The published article by Tillman, cited above, discusses experimental use of a buffered glow discharge consisting of hydrogen and an inert buffer gas, such as argon. This was proposed as a method of reducing undesirable emissions in the hydrogen spectrum. The article states that the buffered discharge is more difficult to regulate and that it probably would operate at a lower hydrogen pressure and consequently have a shorter life due to the "cleanup" of the hydrogen.

To our knowledge, all ultraviolet hygrometers have used hydrogen as the radiation source. More specifically, they use the Lyman-alpha line, which is an emission line of atomic hydrogen found in the far ultraviolet region at 121.56 nm. This line is attractive for hygrometry because of the very strong absorption by water vapor at that wavelength. The absorption of the radiation by water at the Lyman-alpha emission wavelength is several hundred times greater than the corresponding absorption of the radiation by the oxygen in the air. The large absorption coefficient for water vapor results in a significant fraction of the radiation being absorbed within a few millimeters in a hygrometer light path, and a very fast response which can be accurately measured.

All of the literature references relating to spectroscopic hygrometry emphasize the ideal match between the discrimination ratios for absorption of water and oxygen at the Lyman-alpha emission line wavelength and infer that no other emission line is of similar practical value. The present invention arose from experimental substitution of a krypton-filled source tube for the hydrogen tube in order to capitalize on the purity of the krypton emission spectrum and long tube life. Krypton tubes have been available as calibration sources. Because krypton is inert, the gas within the tube does not deteriorate substantially over the tube life.

The substitution of krypton for hydrogen in the hygrometer resulted in new and unexpected results, namely accurate humidity measurements achievable through use of a low power source tube. The tube has long life and can be more accurately calibrated because of its inherent linear operation.

DESCRIPTION OF THE DRAWINGS

A preferred embodiment of this invention is illustrated in the accompanying drawings, in which.

DESCRIPTION OF THE PREFERRED EMBODIMENT

In compliance with the constitutional purpose of the Patent Laws "to promote the progress of science and useful arts" (Article 1, Section 8), applicant submits the following disclosure of the invention.

This invention resides in the substitution of a krypton filled source tube in place of a hydrogen filled source tube conventionally used in measurement of water vapor density by absorption of ultraviolet radiation.

This disclosure pertains to a hygrometer including a krypton-filled glow discharge tube, a detector tube and an intervening gaseous air sample path. It also relates to the method for measuring humidity by generating radiation from a krypton source, directing the radiation to a detector, and passing a sample through the radiation being directed to the detector.

Figure 1:
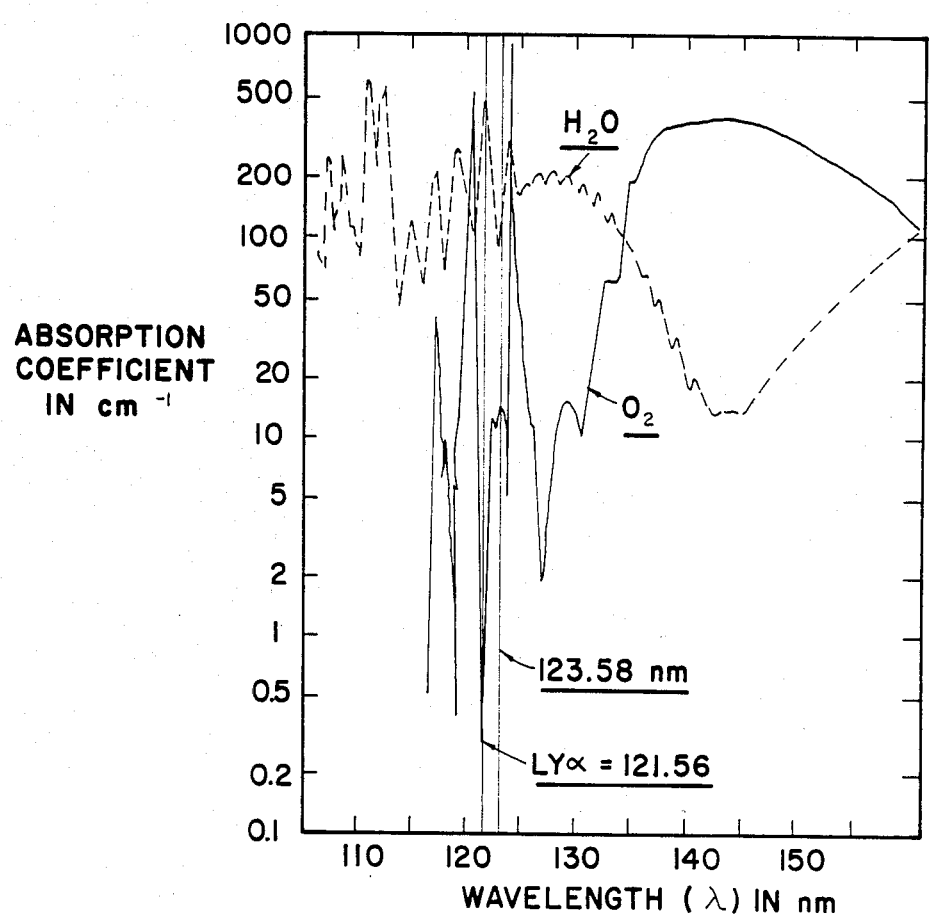
FIG. 1 is a plot of the absorption coefficience of water vapor and oxygen versus wavelength.

FIG. 1 illustrates the absorption coefficients of water and oxygen over the pertinent ultraviolet wavelength spectrum. The relative discrimination ratio (RDR) between the absorption coefficient of water relative to the absorption coefficient of oxygen is at a maximum at approximately 121.56 nm, which coincides with the Lyman-alpha emission line of atomic hydrogen. At this wavelength, the absorption of radiation in water is several hundred times greater than its absorption in oxygen. This permits the effect of oxygen and other background gases to be reduced either automatically or by a simple correction when measuring humidity.

Figure 2:
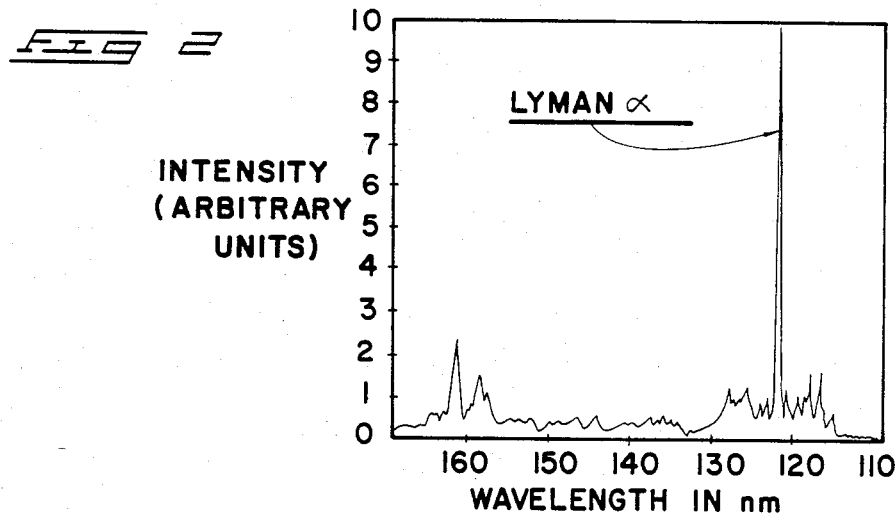
FIG. 2 is a plot of radiation intensity of a hydrogen lamp spectrum in the Lyman-alpha wavelength region.
Figure 3:
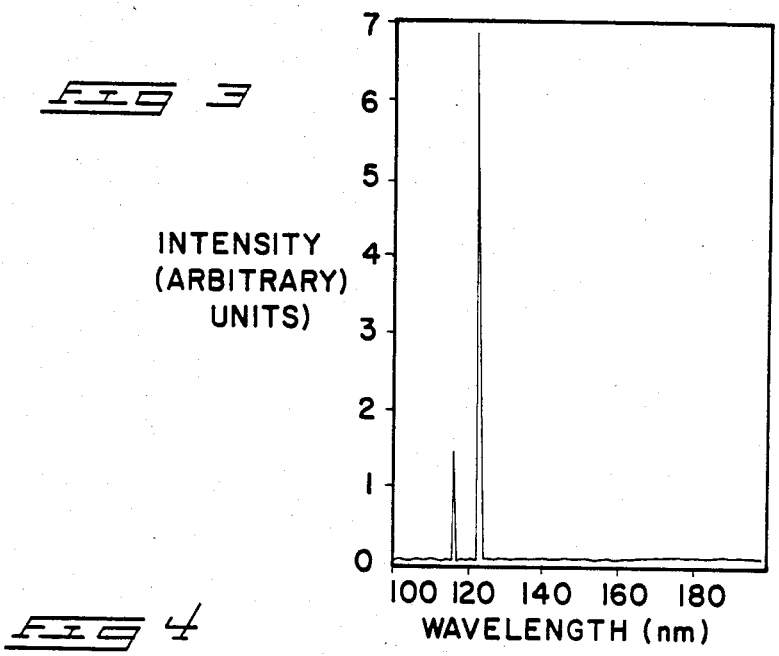
FIG. 3 is a similar plot of the radiation of a krypton lamp spectrum.

FIGS. 2 and 3 are plots of emission intensity in the ultraviolet wavelength spectrum for commercially available hydrogen and krypton lamps. The hydrogen data is based upon emissions from a lamp manufactured by Scientific Services Company of Rocky Hill, New Jersey, and identified as Model 103E. The krypton data is based upon measurements using a lamp from the same company, identified as Model 103C. The wide spectrum of background noise adjacent to the Lyman-alpha emission line produced by hydrogen is very evident from FIG. 2. In contrast, while krypton has one prominent spike at 116.49 nm, the remaining background "noise" is extremely low in comparison to that produced by hydrogen emission.

Figure 4:
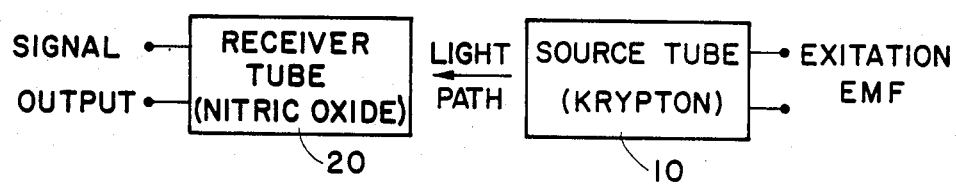
FIG. 4 is a block diagram of the new hygrometer.

As shown in FIG. 4, the hygrometer basically comprises a krypton-filled source tube 10 that directs ultraviolet radiation along a light path leading to a nitric oxide receiver tube 20. The nitric oxide within the tube 20 is thereby ionized in proportion to the amount of radiation that enters it. The resulting radiant flux density is a function of the concentration of water vapor in the path of the radiation between the source tube 10 and receiver tube 20. The ionization within tube 20 produces a small current signal output which can be amplified by an electrometer to produce a usable data signal.

Figure 5:
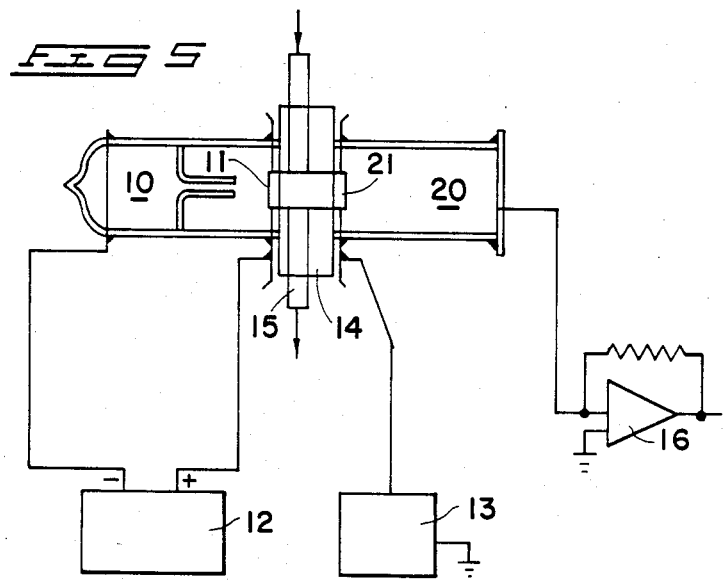
FIG. 5 is a schematic diagram of the hygrometer components.

The hygrometer components are shown schematically in FIG. 5. The krypton glow tube 10 used to date is the Model 103C vacuum ultraviolet lamp manufactured by Scientific Services Company of Rocky Hill, New Jersey. Both tube 10 and the detector tube 20, also manufactured by Scientific Services Company, include a special glass frit seal which we have found to improve the reliability and durability of the hygrometer. Each includes an integral magnesium fluoride window, shown at 11 and 21, respectively. This window attenuates the undesired krypton emission spike at 116.49 nm.

A sample cell 14 is located beween the tubes 10 and 20. It supports tube 15 that permits passage of air samples across the path defined by windows 11 and 21. While not illustrated, the hygrometer can be readily adapted to open path measurements by removing the sample cell 14 to allow free movement of air or other gases between source and detector.

The hygrometer unit is completed by a high voltage battery supply 12 for the krypton tube 10 and a lower voltage battery supply 13 for detector tube 20 and electrometer amplifier 16.

Prior to the discovery of this improvement, it was assumed that the accuracy required of spectroscopic hygrometry required an extremely high ratio between the absorption of radiation by water and oxygen in order to be effective. As can be seen in FIG. 1, the absorption ratio at the 123.58 nm emission line of krypton is approximately 30. Tests to date have shown that this is adequate for achieving accurate humidity measurements comparable to those achieved by use of a hydrogen-filled source lamp.

The use of a krypton source has the advantage that lower pressures can be used in the source tube, since high pressure of the source gas is unnecessary in order to stretch out tube life. The lower pressure enables the tube to produce a spectrum of greater purity than is possible at higher pressures.

We have found that hydrogen glow tubes conventionally used in hygrometers have a life of only a few days when operated continuously. In contrast, the krypton tube identified above has operated continuously for two months without appreciable deterioration of its radiation spectrum. This vastly improves calibration of the hygrometer. While the deterioration of a hydrogen source tube causes unpredictable changes in its nonlinear calibration with time, the krypton tube calibration is substantially linear and evidences very little change with time. Calibration of the krypton hygrometer is readily achieved and very predictable.

The improved apparatus and method described above is subject to modification as the use of krypton is adapted to various configurations of existing hygrometers or further improvements in other hygrometer components. In compliance with the statute, the invention has been described in language more or less specific as to structural features. It is to be understood, however, that the invention is not limited to the specific features shown, since the means and construction herein disclosed comprise a preferred form of putting the invention into effect. The invention is, therefore, claimed in any of its forms or modifications within the proper scope of the appended claims, appropriately interpreted in accordance with the doctrine of equivalents.

We claim:

1. In a hygrometer for measurement of water vapor density by the absorption of ultraviolet radiation, the apparatus comprising:
    a krypton-filled glow discharge tube;
    detector tube means for receiving radiation along a path leading from the glow discharge tube; and
    a gaseous sample path intersecting the path leading from the glow discharge tube to said detector tube means.

2. The hygrometer of claim 1 wherein the krypton-filled glow discharge tube comprises a krypton vacuum ultraviolet lamp.

3. The hygrometer of claim 1 further comprising:
    window means in the path leading from the glow discharge tube to the detector tube for filtering emitted radiation from the krypton tube having a wavelength substantially differing from 123.58 nanometers.

4. The hygrometer of claim 3 wherein the window means are composed of magnesium fluoride ($MgF_2$).

5. A method for measuring water vapor density by the absorption of ultraviolet radiation, comprising the following steps:
    generating ultraviolet radiation from a krypton source having an emission line at a wavelength of 123.58 nanometers;
    directing the generated radiation to a detector for measurement of the radiation received thereby;
    and passing a gaseous sample through the radiation being directed to the detector.

6. The method of claim 5 further comprising the step of filtering the radiation directed to the detector to block passage of radiation having a wavelength substantially differing from 123.58 nanometers.

* * * * *